United States Patent [19]

Louderback et al.

[11] 4,199,471
[45] Apr. 22, 1980

[54] FREEZE-STABLE LIQUID BLOOD CONTROL STANDARD

[76] Inventors: Allan L. Louderback, 9661 Longden Ave., Temple City, Calif. 91780; Paul R. Szatkowski, 24 Winthrop Rd., Bethel, Conn. 06801

[21] Appl. No.: 961,184

[22] Filed: Nov. 16, 1978

[51] Int. Cl.² .......................................... G01N 33/16
[52] U.S. Cl. ................................ 252/408; 23/230 B; 23/928
[58] Field of Search ............... 23/230 B, 928; 252/408

[56] References Cited

U.S. PATENT DOCUMENTS

| 3,876,375 | 4/1975 | Maurukas | 23/230 B |
|---|---|---|---|
| 3,973,913 | 8/1976 | Louderback | 23/230 B |
| 4,056,484 | 11/1977 | Heimburger | 252/408 |
| 4,116,336 | 9/1978 | Sorensen | 252/408 X |
| 4,121,905 | 10/1978 | Maurukas | 252/408 X |
| 4,126,575 | 11/1978 | Louderback | 252/408 |

Primary Examiner—Sidney Marantz

[57] ABSTRACT

A freeze-stable liquid blood control standard and method is provided for the quality control of the measurement of blood pH and gases in the clinical laboratory. The blood control standard comprises a sealed receptacle containing specially treated red cells and a gaseous head space at least equal to about the volume of the red cells. The special treatment comprises thorough washing and separating the red cells from the plasma components and mild treatment with aldehyde, slow admixture with lower aliphatic diol or triol, and retention in a buffered solution. The special treatment optionally includes treating at least a portion of the red cells with carbon monoxide. The head space comprises from 0-15% $CO_2$, 0-25% $O_2$ and the balance $N_2$ and/or inert gas.

17 Claims, No Drawings

FREEZE-STABLE LIQUID BLOOD CONTROL STANDARD

BACKGROUND OF THE INVENTION

This invention relates to a freeze-stable liquid blood control standard which can be used for the quality control of the measurement of blood pH and gases in the clinical laboratory.

Recently, in U.S. Pat. No. 3,973,913, one of the present inventors disclosed a stable blood control standard which comprises a sealed receptacle containing specially treated red blood cells and a gaseous head space having a volume at least equal to about the volume of said red cells. This special treatment comprises thorough washing and separating the red cells from the plasma components and mild treatment with aldehyde and retention in a buffered solution.

While the aforesaid blood control standard remains stable for extended periods of time at temperatures of about 2° to 8° C., it has now been found that substantially better storage stability of the gaseous and liquid phases is obtained by retaining at normally freezing temperatures below 0° C. However, the subsequent thawing of the blood control standard prior to use at above freezing temperatures generally is injurious to the red cell component. Accordingly, it is a principal object of the present invention to provide a blood control standard of the foregoing type which is stable at normally freezing temperatures below 0° C. both with respect to the liquid and gaseous phases and without injury to the red cells upon thawing to above said freezing temperatures.

It is known that glycerol can protect red blood cells against freeze-thaw injury as first reported by Smith, *Lancet* 11, 910 (1950). A more recent summary on the use of glycerol in the freezing of red blood cells is given by Meryman and Hornblower, *Transfusion* 12(3), 145 (1972).

It is also known that glycols such as ethylene glycol can be used for the storage of biological reference control compositions in liquid form at normally freezing temperatures as disclosed in U.S. Pat. No. 3,876,375.

However, the present blood control standard involves a unique composition that employs specially treated red cells in a buffered solution, rather than packed normal red cells, and a gaseous head space which is not contemplated by the aforesaid prior art on storage at freezing temperatures.

BRIEF SUMMARY OF THE INVENTION

In accordance with the present invention, it has now been found that lower aliphatic diols and triols can be employed as cryoprotective agents in a blood control standard of the type disclosed in U.S. Pat. No. 3,973,913 to make it freeze-stable by incorporating said agents into the composition after thorough washing of the aldehyde treated red cells but prior to the admixing with the buffer and gaseous constituents. This improved blood control standard remains stable for extended periods of time, for example, up to 20 months, when stored at about −10° to −25° C. Following the storage at freezing temperatures, the composition can be returned to normal room temperature without injury to the red cell component.

DETAILED DESCRIPTION OF THE INVENTION

The principal fractions of blood are the plasma, red cells or erythrocytes, platelets and white cells. In the average adult human body which contains about 5 liters of blood, the red cells represent about 2.2 liters. In accordance with the present invention, these red cells are first separated from the other blood components and then treated as defined herein.

In order to prevent clotting in storage, whole blood is normally collected in anticoagulant solution such as heparin, EDTA, ACD or CPD solution. Whole blood collected in this manner can normally be stored up to 21 to 28 days without seriously affecting the viability of the residual red cells. Since the end of World War II, the collection and storage of blood has undergone considerable change, and various advances in the separation of the blood components have given rise to the practice of modern blood component therapy. By these procedures, the red cells can be separated from whole blood by sedimentation and centrifugation. The separated red cells can be glycerolized and then stored in a frozen state for subsequent use. Similarly, the separated plasma can also be frozen and stored, or its separated fractions can be frozen and stored for latter use.

In accordance with the present invention, any of the above sources of red cells, fresh or outdated cells (cells stored in excess of 21 to 28 days) can be employed. These cells can be derived from human or other mammalian sources including, for example, equine, bovine, porcine, and sheep species.

In order to ensure complete separation from the other blood components, the red cells are sedimented or centrifuged and thoroughly washed. Sedimentation is facilitated by spinning in a conventional blood centrifuge. Centrifuges for such blood cell sedimentation are well-known, and a continuous flow type centrifuge such as is commercially available from the Haemonetics Corp. is preferred. Centrifuges of this type are described, for example, in U.S. Pat. No. 3,706,412. In this type of centrifuge, the bowl has two parts, one that rotates and another that is stationary. As the blood or previously separated red cells enter the spinning bowl, the cells are distributed to the periphery and as the bowl fills, the supernatant separates from the red cells. The red cells are held in suspension by centrifugal force while the supernatant is expelled through an effluent port into a waste collection receptacle.

A washing solution is then made to follow the same path as the red cells. The washing solution is a saline solution which preferably is normal physiological saline containing about 0.9% NaCl but can also contain other substances such as, for example, the components of Alsever's solution. The geometry of the centrifuge keeps the cells circulating against the flow of fresh wash solution as the used wash solution is expelled through the effluent port. When the washing is complete, the centrifuge is stopped and the washed cells are siphoned into a separate collection vessel.

Another example of a conventional blood centrifuge that is suitable for use in the invention is the Celltrifuge separator which is commercially available from the American Instrument Company.

In the foregoing washing procedures, the red cells are preferably washed with from about 5 to about 30 volumes of the saline washing solution. In a preferred example, a unit of blood (one pint) is washed with about 3–4 liters of saline.

Following the saline washing, the red cells are ready for the mild treatment with aldehyde. If not treated immediately, it is preferred to temporarily store the cells in Alsever's solution. This solution can be prepared by admixing the following components in the stated amounts and diluting with water to a volume of three liters:

| Component | Amount |
| --- | --- |
| Glucose (dextrose) | 61.5 grams |
| Sodium citrate | 24.0 grams |
| Sodium chloride | 12.6 grams |
| Citric acid (1% solution) | 15.6 ml. |
| Neomycin | 300 mg |
| Chloramphenicol | 990 mg |

The components should be mixed well and the pH adjusted to within a range of about 6.4 to 6.8. The washed red cells can be retained in the Alsever's solution for about 45 days at 2° to 8° C.

The washed red cells, when ready for the aldehyde treatment, are first re-suspended in saline solution in proportions of about one part by volume of cells to about 5 to 30 parts by volume of the saline. The mild treatment with aldehyde which follows comprises the relatively slow addition of a saline solution of the aldehyde to the cells and admixing at room temperature and generally within the range of about 20° to about 26° C. The aldehyde solution preferably ranges from about 0.1 to about 0.6 molar aldehyde in saline. Aldehyde substances which are employed in the aldehyde/-saline solution generally are aliphatic aldehydes having from one to about six carbon atoms, such as, for example, formaldehyde, acetaldehyde, propionaldehyde, butyraldehyde, malonic aldehyde, succinaldehyde, glutaraldehyde, and pyruvic aldehyde. The saline preferably is normal physiological saline and the aldehyde preferably is a monoaldehyde, especially formaldehyde. The suspension of the red cells in the aldehyde/-saline solution is mixed such as by stirring for about 15 minutes to about 4 hours, preferably about 60 minutes, during which time the cells take on a bright red appearance which resembles fresh arterial blood.

Following the mild treatment with aldehyde, the treated cells are sedimented such as by centrifugation and again washed with saline in about the same range of proportions as in the initial saline washing, although washing with less saline, e.g., 2–3 liters of saline per unit of blood, also is suitable.

As before, the red cells can be used directly in the next step or the cells can be temporarily stored in Alsever's solution at 2° to 8° C.

After completion of the aldehyde treatment, the red cells are transferred to a suitable receptacle for admixture with lower aliphatic diol or triol. As used herein, the term lower means having from 2 to 5 carbon atoms. Suitable such diols and triols are, for example, ethylene glycol, propylene glycol, propane 1,3diol, butanediol, pentanediol, and glycerol. Of these, ethylene glycol is the preferred cryoprotective agent.

It is important to the invention that the admixing of the aldehyde treated red cells with the diol or triol cryoprotective agent be carried out gradually or incrementally over an extended period of time to allow the red cells to accomodate themselves to the continuously changing environment without disrupting the chemical integrity and morphology of the cells. During this slow admixing, the cryoprotective agent progressively penetrates the cell structure.

By the appropriate sequence of admixing the aldehyde treated red cells with the cryoprotective agent and the slow admixing, the blood control standard of this invention retains its liquid constituency at normally freezing temperatures of $-10°$ to $-25°$ C. and it can be returned to normal room temperatures without cell disruption which would otherwise be caused by said thawing.

The concentration of the cryoprotective agent used in admixture with the red cells preferably with vary from about 20% to 40% and most preferably about 33% by volume of the total composition. For example, one volume of red cells can be diluted by slow addition of one-half volume of ethylene glycol with constant mixing over a time period of about 15 to 20 minutes to provide a $33\frac{1}{3}\%$ concentration of the cryoprotective agent.

Following addition of the cryoprotective agent, the treated red cells or any portion thereof can be saturated with carbon monoxide in those cases in which the blood control standard is desired for use with an instrument designed to provide assay of the carbon monoxide/-hemoglobin (carboxyhemoglobin) content of the blood samples. The optional treatment with carbon monoxide can be carried out as described in co-pending application Ser. No. 853,928, filed Nov. 22, 1977. This can be done by saturating the red cells in a saline solution with carbon monoxide for a period of about 15 to 30 minutes with continuous stirring. After saturation, the carbon monoxide saturated red cells can be combined in any desired proportions with other red cells which have not been thus saturated with carbon monoxide. For example, 5 parts of the CO saturated red cells can be combined with 95 parts of the non-CO saturated red cells to provide a 5% CO red cell combination.

After addition of the desired cryoprotective agent and, optionally, admixture with CO, the red cells are preferably buffered and transferred into suitable receptacles which are capable of being sealed so as to be completely gas tight from the ambient atmosphere. These receptacles can be, for example, glass ampules, vials or bottles.

The buffering of the cells, while not necessary, is such as to maintain a desired pH of from about 7 to about 7.7 depending upon whether the blood control standard is to be representative of the normal range, acidosis or alkalosis. The normal range is about $7.4\pm0.1$ while the acidosis is 7.0–7.3 and alkalosis is $7.6\pm0.1$. The molarity of the buffer preferably is from about 0.05 to about 0.2 molar. Conventional buffer materials such as, for example, phosphate and tris buffers can be used, but phosphate is generally useful only at pH below 7.5 while tris is generally useful only at pH above 7.5. Preferred buffer materials for maintaining the desired pH are N-tris(hydroxymethyl)methyl-2-aminoethanesulfonic acid (TES) and N-2-hydroxyethylpiperazine-N'-2-ethanesulfonic acid (HEPES). These and other such suitable buffer materials are described by Good et al., *Biochemistry* 5, 467–77 (1966).

Sufficient bicarbonate ion, for example, $NaHCO_3$, also is added to the red cells to bring the $pCO_2$ preferably to a level of from about 20 to about 55 mm Hg, although higher levels, e.g., 77–82 mg Hg, also are suitable.

It should be understood that the aforesaid steps of buffering and addition of bicarbonate ion can be carried out prior to the optional admixture with carbon monoxide. In such case it may be desirable to readjust the pH and $pCO_2$ in a small amount to the aforesaid preferred levels after the CO addition.

The buffered cells are placed into the receptacles to a level such as to leave a head space at least equal to about the volume of the red cells. Larger volumes of head space can be used, for example, up to 50 times the volume of red cells. This head space is then filled with a gas or a mixture of gases comprising 0–15% $CO_2$, 0–25% $O_2$ and the balance $N_2$ and/or inert gas. As used herein, the term inert gas refers to any gas which is inert to the reactions which take place in the electrode systems of the blood pH and gas analyzer instruments. This includes the so-called inert gases which have a completed group of electrons in their outermost shells, for example, He, Ne, Ar, Kr, Xe and Rn. These gases can be added from separate gas sources or as a preadmixture of the desired gases.

The electrodes referred to above are the conventional pH, $pCO_2$ and $pO_2$ electrodes used in the blood pH and gas analysis instruments described hereinbefore. For example, the hydrogen ion concentration may be monitored with a pH responsive glass electrode in cooperation with a Ag/AgCl reference electrode, the partial pressure of carbon dioxide may be sensed in the circulating fluid by a $CO_2$ electrode and the oxygen may be monitored with an oxygen-sensing electrode.

In order to ensure that the blood control standard will be saturated with the desired gas, the gas preferably is flushed into the receptacle in a volume of from about 10 to about 60 times the volume of the receptacle and the receptacle is then immediately sealed before any significant exchange with atmosphere gas can take place. The desired gas tight sealing can be achieved, for example, by using a glass ampule as the receptacle and melting the top of the ampule in a flame to provide a flame-sealed closure. In the case of vials or bottles, other types of conventional hermetic sealing can be employed.

The gases in the sealed receptacle will then come into equilibrium with the red cells to provide, in essence, a miniature tonometer. This final product remains stable and provides the desired pH, $pO_2$ and $pCO_2$ values for extended periods, for example, up to six months, when stored at about 2° to 8° C. However, the product also can be stored at normally freezing temperatures below 0° C. for substantially longer periods with further improved stability of the components. The presence of the red cells also supplies hemoglobin to the blood control standard and, thereby, enables the determination of Base Excess, from which one can calculate $O_2$ content and $O_2$ saturation.

Prior to actual use, the blood control standard is returned to normal room temperature and treated to eliminate extraneous errors of ambient room temperature and sample handling by incubating at 37° C. in a water bath to (a) physiologically prepare the sample to that of body temperature, (b) to fully equilibrate the sample with the sealed gases, and (c) to prepare the sample to resemble a freshly withdrawn arterial specimen. This can be done by incubating in the water at 37° C. for about 30 minutes prior to use or by incubating at 37° C. for at least about three minutes and then shaking under the water for about ½ to one minute just prior to use.

Since the measurement of blood gases follows the principles of the natural gas laws, temperature is somewhat critical if the sample is to be fully equilibrated to obtain the correct partial pressures. Upon completion of incubation, the ampule is broken, and the control sample can be directly aspirated or drawn into a syringe for direct presentation to a blood gas analyzer and/or oximeter instrument.

The following detailed examples will further illustrate the invention although it will be appreciated that the invention is not limited to these specific examples.

EXAMPLE 1

A unit (one pint) of fresh human blood collected in ACD or CPD anticoagulant solution is expressed into a Haemonetics Corp. continuous flow centrifuge. As the blood enters the centrifuge, the red cells are distributed to the periphery and the supernatant is expelled through the effluent port. While spinning, the cells are washed with 3 to 4 liters of a washing solution comprising an aqueous solution of 0.9% NaCl (normal physiological saline). The washed red cells are siphoned into a collection vessel and then transferred to a vessel containing five liters of normal physiological saline. To the red cells/saline mixture at 25° C. is then added slowly over a brief time period of 5 to 10 minutes 500 ml of saline containing 40 ml of formaldehyde (37%) solution to thereby provide a 0.1 molar formaldehyde in 0.9% NaCl solution. The mixture is stirred at 25° C. for 60 minutes, during which time the cells assume a bright red color resembling fresh arterial blood. The formaldehyde treated cell mixture is then transferred to the continuous flow centrifuge wherein the cells are further washed with 6 to 8 liters of 0.9% saline solution. The washed cells are then siphoned into a collection vessel and placed on a magnetic stirrer. Ethylene glycol is then added slowly with stirring over a 15 minute period in an amount equal to one-half (½) the volume of the red cells to provide a final concentration of ethylene glycol of 33⅓ volume %. The glycol treated cells are then buffered with an aqueous solution of 0.1 molar HEPES. Sufficient $NaHCO_3$ solution is then added to adjust the $pCO_2$ to 40 mm Hg. The pH is given a final adjustment to 7.4. The buffered red cells are then transferred in two ml. aliquots into glass ampules (Wheaton No. 1 glass), each having a capacity of 8 ml. A premixed gas containing 5% $CO_2$, 12% $O_2$ and 83% $N_2$ is then flushed into the ampules at the rate of 600 ml. of gas. The ampules are immediately sealed by rotating the top in a flame and pulling off the tip.

EXAMPLE 2

A unit (one pint) of fresh human blood collected in ACD or CPD anticoagulant solution is expressed into a Haemonetics Corp. continuous flow centrifuge. As the blood enters the centrifuge, the red cells are distributed to the periphery and the supernatant is expelled through the effluent port. While spinning, the cells are washed with 3 to 4 liters of a washing solution comprising an aqueous solution of 0.9% NaCl (normal physiological saline). The washed red cells are siphoned into a collection vessel and then transferred to a vessel containing five liters of normal physiological saline. The red cells/saline mixture at 25° C. is then added slowly over a brief time period of 5 to 10 minutes 500 ml of saline containing 40 ml of formaldehyde (37%) solution to thereby provide a 0.1 molar formaldehyde in 0.9% NaCl solution. The mixture is stirred at 25° C. for 60 minutes, during which time the cells assume a bright red color resembling fresh arterial blood. The formaldehyde treated cell mixture is then transferred to the continuous flow centrifuge wherein the cells are further washed with 6 to 8 liters of 0.9% saline solution. The washed cells are then siphoned into a collection vessel and placed on a magnetic stirrer. Ethylene glycol is then added slowly with stirring over a 15 minute period in an amount equal to one-half (½) the volume of the red cells to provide a final concentration of ethylene glycol of 33⅓ volume %. The glycol treated cells are then buffered with an aqueous solution of 0.1 molar HEPES.

A portion of the resultant is then completely saturated with carbon monoxide for a period of 15 to 30 minutes with continuous stirring. Five parts of which saturated material are combined with 95 parts of the unsaturated portion. Also, in a similar manner 10 parts of such saturated material are combined with 90 parts of the saturated parts. Also, any number of parts of the carbon monoxide portion is mixed with (100-any) parts of the concentrate portion to give 5%, 10% and/or any carbon monoxide levels, respectively.

Sufficient $NaHCO_3$ solution is then added to adjust the $pCO_2$ to 40 mm Hg. The Ph is given a final adjustment to 7.4. The buffered red cells are then transferred in two ml. aliquots into glass ampules (Wheaton No. 1 glass), each having a capacity of 8 ml. A premixed gas containing 5% $CO_2$, 12% $O_2$ and 83% $N_2$ is then flushed into the ampules at the rate of 600 ml. per 60 seconds, each ampule being flushed with 150 ml. of gas. The ampules are immediately sealed by rotating the top in a flame and pulling off the tip.

Various other examples will be apparent to the person skilled in the art after reading the foregoing description without departing from the spirit and scope of the invention and it is intended that all such examples be included within the scope of the appended claims.

What is claimed is:

1. A freeze-stable blood control standard for the quality control of the measurement of blood pH and gases comprising a sealed receptacle containing treated erythrocytes and a gaseous head space having a volume which is at least equal to about the volume of said erythrocytes, said erythrocytes being treated by thorough washing in saline solution, mild admixing with a solution of aldehyde and saline, thorough washing in saline solution, then slow admixing with a cryoprotective agent selected from the group consisting of lower aliphatic diols and triols to a concentration of from about 20 to about 40 volume percent of said cryoprotective agent, said gaseous head space comprising from about 0% to about 15% $CO_2$, from about 0% to about 25% $O_2$ and the balance selected from the group consisting of $N_2$ and inert gases and mixtures thereof.

2. The freeze-stable blood control standard of claim 1 in which the cryoprotective agent is ethylene glycol.

3. The freeze-stable blood control standard of claim 2 in which the ethylene glycol concentration is about one-half the volume of the erythrocytes.

4. The freeze-stable blood control standard of claim 1 wherein the erythrocytes are buffered to a pH of from about 7 to about 7.7 and admixed with bicarbonate ion to a $pCO_2$ of from about 20 to about 55 mm Hg.

5. The freeze-stable blood control standard of claim 4 in which the buffer is selected from the group consisting of HEPES and TES buffers.

6. The freeze-stable blood control standard of claim 1 in which the aldehyde is an aliphatic aldehyde having from 1 to about 6 carbon atoms.

7. The freeze-stable blood control standard of claim 6 in which the aldehyde is formaldehyde.

8. The freeze-stable blood control standard of claim 1 in which the aldehyde concentration is from about 0.1 to about 0.6 molar.

9. The freeze-stable blood control standard of claim 1 in which the mild admixing with aldehyde is at about 20° to about 26° C. for about 15 minutes to about 4 hours.

10. The freeze-stable blood control standard of claim 1 in which at least a portion of the erythrocytes are treated with carbon monoxide and then combined with that portion of the erythrocytes that have been untreated with carbon monoxide.

11. The freeze-stable blood control standard of claim 1 in which the saline is normal physiological saline.

12. The freeze-stable blood control standard of claim 1 in which the erythrocytes are buffered to a pH of from about 7 to about 7.7, and in which at last a portion of the erythrocytes are treated with carbon monoxide and then combined with that portion of the erythrocytes that have been untreated with carbon monoxide and admixed with bicarbonate ion to a $pCO_2$ of from about 20 to about 55 mm Hg.

13. The freeze-stable blood control standard of claim 12 in which the cryoprotective agent is ethylene glycol.

14. The freeze-stable blood control standard of claim 12 in which the aldehyde is formaldehyde.

15. The freeze-stable blood control standard of claim 12 in which the saline is normal physiological saline.

16. The method of making a freeze-stable blood control standard for the quality control of the measurement of blood pH and gases comprising thoroughly washing erythrocytes in saline solution, mildly admixing with a solution of aldehyde and saline, thoroughly washing in saline solution, then slowly admixing with a cryoprotective agent selected from the group consisting of lower aliphatic diols and triols to a concentration of from about 20 to about 40 volume percent of said cryoprotective agent, transferring to receptacles while leaving a gaseous head space of at least about equal to the volume of said erythrocytes, flushing said head space with a gas comprising from about 0% to about 15% $CO_2$, from about 0% to about 25% $O_2$ and the balance selected from the group consisting of $N_2$ and inert gases and mixtures thereof, and immediately thereafter sealing said receptacles to form a gas tight closure.

17. The method of claim 16 in which following the admixing with the cryoprotective agent the erythrocytes are buffered to a pH of from about 7 to about 7.7, and in which at least a portion of the erythrocytes are treated with carbon monoxide and then combined with that portion of the erythrocytes that have been untreated with carbon monoxide and admixed with bicarbonate ion to a $pCO_2$ of from about 20 to about 55 mm Hg.

* * * * *